US006270985B1

(12) United States Patent
Gottschalk et al.

(10) Patent No.: US 6,270,985 B1
(45) Date of Patent: Aug. 7, 2001

(54) ELISA SERODIAGNOSIS OF PIG PLEUROPNEUMONIA SEROTYPES 5A AND 5B

(75) Inventors: Marcelo Gottschalk, St-Charles-sur-Richelieu; Daniel Dubreuil, Montréal; Réal Lallier, Ste-Hyacinthe, all of (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/253,678

(22) Filed: Feb. 19, 1999

Related U.S. Application Data

(63) Continuation-in-part of application No. 08/507,200, filed on Jul. 26, 1995, now abandoned.

(51) Int. Cl.[7] .................. G01N 33/542; G01N 33/53; G01N 33/574; G01N 33/537; C12Q 1/04
(52) U.S. Cl. .................. 435/7.9; 435/7.2; 435/7.32; 435/7.92; 435/7.93; 435/29; 435/34; 435/967; 435/975; 530/387.1; 530/388.4
(58) Field of Search .................. 435/7.9, 7.2, 7.32, 435/7.92, 7.93, 34, 29, 967, 975; 530/387.1, 388.4

(56) References Cited

U.S. PATENT DOCUMENTS

| | | | |
|---|---|---|---|
| 4,182,856 | * | 1/1980 | Buckler et al. . |
| 4,698,298 | * | 10/1987 | Dedieu et al. . |
| 4,745,074 | | 5/1988 | Schreuer et al. . |
| 4,774,177 | | 9/1988 | Marks . |
| 4,814,269 | | 3/1989 | Karpas . |
| 4,839,298 | | 6/1989 | Kay et al. . |
| 4,954,630 | * | 9/1990 | Klein et al. . |
| 5,010,017 | * | 4/1991 | Ferrua et al. . |
| 5,013,646 | | 5/1991 | Woiszwillo . |
| 5,149,627 | * | 9/1992 | Brown . |
| 5,156,948 | | 10/1992 | Christensen et al. . |
| 5,304,645 | * | 4/1994 | Klein et al. . |
| 5,648,227 | | 7/1997 | Basboll . |

FOREIGN PATENT DOCUMENTS

| | | | |
|---|---|---|---|
| 276686 | * | 7/1992 | (CS) . |
| 0875760 | * | 11/1998 | (EP) . |
| 02176464 | * | 7/1990 | (JP) . |
| WO 97/03361 | * | 1/1997 | (WO) . |
| WO 97/46883 | * | 12/1997 | (WO) . |

OTHER PUBLICATIONS

Bossé J. et al., 1990, Can J. Vet. Res., 54:427–431.
Goyette G. et al., 1986, Int. Pig. Vet. Soc. Proc., 9:258.
Inzana T. and Mathison T., 1987, Infect. Immun., 55:1580–1587.
Mittal K. et al., 1984, Am. J. Vet. Res., 45:715–719.
Nadeau M. and Higgins R., 1991, Bulletin Épidémiologique, 2:4–5.
Perry B. et al., 1990, Sero. Immunol. Infect. Dis., 4:299–308.
Gottschalk M. et al., 1994, Vet. Microbiol., 42:91–104.
Trottier Y.L. et al., 1992, J. Clin. Microbiol., 30:46–53.
Altman et al., 1992, Eur. J. Biochem., 204:225–230.
Altman et al., 1990, Cell. Biol. 68:1268–1271.
Bossé et al., 1990, Can. J. Res., 54:320–325.
Fenwick and Osburn, 1986, Infect. Immun., 54:575–582.
Radacovici et al., 1992, Vet. Microbiol., 30:369–385.
Gray B.M., 1979, J. Immun. Methods, 28;187–192.
Joshi et al, Mol. Immunol., 29/7–8:971–981, 1992.*
Fenwick et al, Infection and Immunity, 53/2:298–304.*
Malvano et al, Dev. Clin. Biochem., 1(Immunoenzym. Assay Tech.):59–74, 1980.*
Fenwick et al, Infection and Immunity, 54/2:583–586, 1986.*
Mittal et al, J. Clin. Microbiol., 29/7:1344–1347, 1991.*
MacInnes et al, Can. J. Vet. Res., 54:244–250, 1990.*
Ma et al, J. Clin. Microbiol., 28/6:1356–1361, 1990.*
Willson et al, Can. Vet. J., 28:111–116, 1987.*
Inzana et al, Vet. Microbiol., 31:351–362, 1992.*
Nielsen et al., J Clin Microbio., 1991, 29: 794–7.
Neilsen et al., Vet Microbio, 1995, 43: 277–81.
Altman et al., Carbohydrate Res, 1989, 191: 295–30.
Altman et al., Biochem Cell Biol, 1988, 66: 998–1004.
Benyon et al, Carbohydrate Res, 1991, 209: 211–23.
Nielsen et al., Res Vet Sci., 1993, 54: 57–62.

* cited by examiner

Primary Examiner—Nita Minnifield
(74) Attorney, Agent, or Firm—Klauber & Jackson

(57) ABSTRACT

The present invention relates to an ELISA diagnostic kit for the assay of A. pleuropneumoniae serotypes 5a and 5b antibodies in the serum of pigs comprising in separate packaging, at least one of the following: a) a plate or solid support having bound thereto a purified lipopolysaccharide A. pleuropneumoniae serotype 5 antigen for a specific binding to anti-A. pleuropneumoniae serotypes 5a or 5b antibodies present in the serum of pigs; b) serum from pigs experimentally inoculated with a strain of A. pleuropneumoniae serotypes 5 to serve as a positive control; c) pig serum from A. pleuropneumoniae free herd to serve as a negative control; and d) a detectably labeled conjugate which bind to pigs antibodies bound to the plate of a).

18 Claims, 1 Drawing Sheet

BL = Blanks
CP = Positive control
CN = Negative control
S1 to S40 = serum to be analyzed

ELISA SERODIAGNOSIS OF PIG PLEUROPNEUMONIA SEROTYPES 5A AND 5B

RELATED APPLICATION

This application is a continuation-in-part of application Ser. No. 08/507,200 filed on Jul. 26, 1995 now abandoned, which is hereby incorporated by reference in its entirety.

BACKGROUND OF THE INVENTION (a) Field of the Invention

The invention relates to kits for the accurate, rapid and sensitive assay of *A. pleuropneumoniae* serotypes 5a and 5b antibodies in pig serum for swine pleuropneumonia serodiagnosis.

(b) Description of Prior Art

*Actinobacillus pleuropneumoniae* is known as one of the most pathogenic agent of the respiratory tract of swine. Swine pleuropneumonia is still an important problem in large swine operations, causing serious economic losses in this industry. Since the presence of *A. pleuropneumoniae* is often unnoticed in chronically infected herds, the identification of carrier animals is a main concern. Following a stressful situation, several clinically fatal cases may arise in a given herd. Infection in swine can be fatal but animals surviving the infection frequently become carriers. Detection of chronically infected carriers is crucial since those animals act as reservoirs of infection. Since the infection is often unnoticed, serology become a useful tool for the detection of chronic infection. Several studies indicate that it is possible to control or eliminate the infection in certain herds based on the serological results.

Various serological assays for *A. pleuropneumoniae* have been described. Among others, the complement fixation test (CFT), the enzyme-linked immunosorbent assay (ELISA); (Goyette G. et al., 1986, *Int. Pig. Vet. Soc. Proc.,* 9:258) and the 2-mercapto-ethanol tube agglutination test (Mittal, K. et al., 1984, *Am. J. Vet. Res.,* 45:715–719) have been used. Out of the different assays, the ELISA is often the most useful since it is faster and easier to perform. On the other hand, up to now, the results obtained suggested the use of a more purified antigenic preparation in order to improve the specificity of the test.

A saline extract of boiled-formalinized whole cells of *A. pleuropneumoniae* (also called crude extract) is presently used, in some laboratories, as the antigen for ELISA serodiagnosis (Goyette G. et al., 1986, *Int. Pig. Vet. Soc. Proc.,* 9:.258). Standardization of the assay is complicated as variations are noticed between extracts.

Using different antigen preparations, cross-reactions among serotypes and with other bacterial species were also reported (Bossé, J. et al., 1990, *Can. J. Vet. Res.,* 54:427–431). Although the capsular polysaccharide (CPS) of *A. pleuropneumoniae* has been shown to be responsible for serotype specificity (Inzana, T. and Mathison, T., 1987, *Infect. Immun.,* 55:1580–1587), the difficulty of obtaining pure CPS in large quantity precludes its utilization for serodiagrrostic purposes. The CPS were very unstable and were fixed with difficulty to the walls of the polystyrene plate used in the ELISA assay (Perry, B. et al., 1990, *Sero. Immunol. Infect. Dis.,* 4:299–308).

Serology, which is used to identify animals that have developed an immune response to specific pathogens, is an important tool in disease management and prevention of *A. pleuropneumoniae* infection in pigs. The importance of serological testing is further emphasized by the lack of a vaccine that reliably prevents infection. The demand of pigs from *A. pleuropneumoniae* sero-negative herds is increasing, especially from producers whose herds have experienced acute outbreaks of the disease and who have decided to "eradicate" *A. pleuropneumoniae*, buying only sero-negative animals (coming from sero-negative herds) for the replacement. A successful eradication program depends mostly on the accuracy and reliability of the serological tests used to identify *A. pleuropneumoniae* infected pigs. Nevertheless, interpretation of serology should be done cautiously. A test that is not sensitive will not detect all infected herds or animals (false negative results) and one that is not specific will erroneously condemn some non-infected animals (false positive results).

The antigenic specificity of *A. pleuropneumoniae* serotype 5 appears to be linked, at least partly, to the capsular polysaccharides (Altman et al., 1992, *Eur. J. Biochem.* 204:225–230; Bosse et al., 1990a, *Can. J. Res.* 54:320–325, and 1990b, *Can. J. Vet. Res.* 54:427–431) or, according to other authors, to the smooth lipolysaccharides (Altman et al., 1990, *Cell. Biol.* 68:1268–1271; Fenwick and Osburn, 1986, *Infect. Immun.* 54:575–582; Radacovici et al., 1992). However, these capsular polysaccharides turn out to be very unstable and are difficult to attach to the polystyrene surfaces of the plates used for the ELISA (Perry et al., 1990, *Immunother. Infect. Dis.* 4:299–308; Gray B. M., 1979, *J. Immun. Methods,* 28:187–192). The antigenic specificity of *A. pleuropneumoniae* mainly comes from the capsular polysaccharides, which are not very immunogenic. Purified capsular polysaccharides antigens are very difficult to obtain and, in addition, contamination with non-specific antigen are very common. The distinction between these serotypes (5a/5b) necessitate bacterial isolation. The isolation of the bacteria from chronically infected animals is a time consuming and low sensitive method.

The use of antibiotics is mainly useful to control the mortality, but it has no real benefit on pigs with chronic pleuropneumonia. Treated animals often continue to carry the organism and can be a source of infection for other animals. In addition, an increasing number of strains resistant to different antimicrobials has been observed in the last years in Quebec (Nadeau, M. and Higgins, R., 1991, *Bulletin épidémiologique,* 2:4–5).

There are some cross-reactions among serotypes; for example: serotypes 3, 6 and 8, serotypes 1, 9 and 11, and serotypes 7 and 4. In addition, other cross-reactions, which are not found in serotyping, could be observed in serological analysis of chronically infected animals that are continuously challenged with the microorganism. These cross-reactions are usually associated with outer membrane proteins (cell wall proteins, iron-repressible proteins, etc.) and rough lipopolysaccharides. However, it is important to remember that one herd, and even one animal, might be infected with several serotypes simultaneously. In this case, the detected antibodies against different serotypes are probably not cross-reactions, but homologous and specific reactions. This is one of the most important problem to be solved by the use of specific and sensitive serological tests in accordance with the present invention.

Healthy carrier pigs may be responsible for the transmission of the disease. The absence of clinical signs and/or lesions at the slaughter-house does not implicate necessarily the absence of the infection.

Following infection, antibodies can usually be detected in 10–15 days. Some animals will remain serologically positive for a few months, but most will be positive for a long period of time; once more, it will depend on the test used.

The proportion of seropositive sows as well as their titers tended to decrease with age.

Isolation of *A. pleuropneumoniae* from apparently healthy carrier pigs is difficult; it probably should be used as a complement to the serology in conflictive cases.

The development of better serological tests is a necessity because the infection still has an economic impact on the swine industry and the current vaccines are not effective.

To date, there exist no stable kit for the effective serodiagnosis of pig pleuropneumonia in the field.

It would be highly desirable to be provided with a kit for readily determining the presence of antibodies against *A. pleuropneumoniae* serotypes 5a and 5b in a serum sample.

It would be highly desirable to be provided with an ELISA diagnostic kit for *A. pleuropneumoniae* which could be used for *A. pleuropneumoniae* serodiagnosis while remaining in the field.

SUMMARY OF THE INVENTION

One aim of the present invention is to provide a kit for the accurate, rapid and sensitive assay of antibodies against *A. pleuropneumoniae* serotypes 5a and 5b in a sample.

Another aim of the present invention is to provide an ELISA diagnostic kit for *A. pleuropneumoniae* to be used for *A. pleuropneumoniae* serodiagnosis while remaining in the field. The novelty and originality of the ELISA diagnostic kit of the present invention resides in the particular combination of a novel purification method of the antigen to be used and a novel sensitization and stabilization methods of the plates of the kit.

The kits of the present invention differs from the ELISA method of the prior art for the determination of *A. pleuropneumoniae* antibodies. In the prior art method, the antigen is fixed to the plates in a PBS buffer and the plates are immediately used after the antigen fixation is completed. The prior art method may include a computerized reading protocol for the determination of the antibodies in the samples as described by Trottier, Y. L. et al. (1992, *J. Clin. Microbiol.*, 30:46–53). The kits of the present invention mainly differ in that the antigen is purified using a higher concentration of phenol and the antigen fixation procedure is different. Indeed, the purified antigen is resuspended in a PBS-EDTA buffer which is then added to each well of the plate. After an 18 hour incubation, a horseradish peroxidase (HRP) conjugate stabilizing solution (sold by Calbiochem-Novabiochem Corporation, La Jolla, Calif. 92039, U.S.A., catalogue #516534, containing phosphate buffered saline pH 7.2, BSA, 0.1% thimerosal and caprylic acid) is added to each well. The antibodies in the samples are determined visually by adding a chromogen, preferably 3,3',5,5'-tetramethylbenzidine, e.g. TMBlue™ (Biovest Inc., Massachusetts, USA) (see U.S. Pat. No. 5,013,646, issued May 7, 1991). The kits of the present invention, when compared to the prior art ELISA method, demonstrate a relative sensitivity and a relative specificity of 100%.

In accordance with another embodiment of the present invention there is provided an ELISA diagnostic kit for the assay of *A. pleuropneumoniae* serotypes 5a or 5b antibodies in the serum of pigs comprising in separate packaging, at least one of the following:

a) a plate or solid support having bound thereto a purified lipopolysaccharide *A. pleuropneumoniae* serotype 5 antigen for a specific binding to anti-*A. pleuropneumoniae* serotypes 5a or 5b antibodies present in the serum of pigs;

b) serum from pigs experimentally inoculated with a strain of *A. pleuropneumoniae* serotypes 5 to serve as a positive control;

c) pig serum from a specific pathogen free herd to serve as a negative control; and d) a detectably labeled conjugate which bind to pigs antibodies bound to the plate of a).

The ELISA diagnostic kits of the present invention may further comprise the following:

e) a substrate which allow the visualization of the detectably labeled conjugate.

In accordance with another embodiment of the present invention there is provided a method for the preparation of the kit, which comprises the steps of:

a) purifying lipopolysaccharide *A. pleuropneumoniae* serotype 5 antigen by phenol extraction and centrifugation of said antigen bacterial crude extract;

b) fixing the antigen of step a) to a solid support and stabilizing said fixed antigen;

C) immunizing mammals with a strain of *A. pleuropneumoniae* serotype 5 and collecting serum to serve as positive control sera; and d) collecting sera from *A. pleuropneumoniae* free herds to serve as negative control sera.

In a particular embodiment the HRP conjugate stabilizing solution contains phosphate buffered saline pH 7.2, 20 mg/ml BSA, 0.1% thimerosal and a saturating amount of caprylic acid.

DETAILED DESCRIPTION OF THE INVENTION

Figure 1:
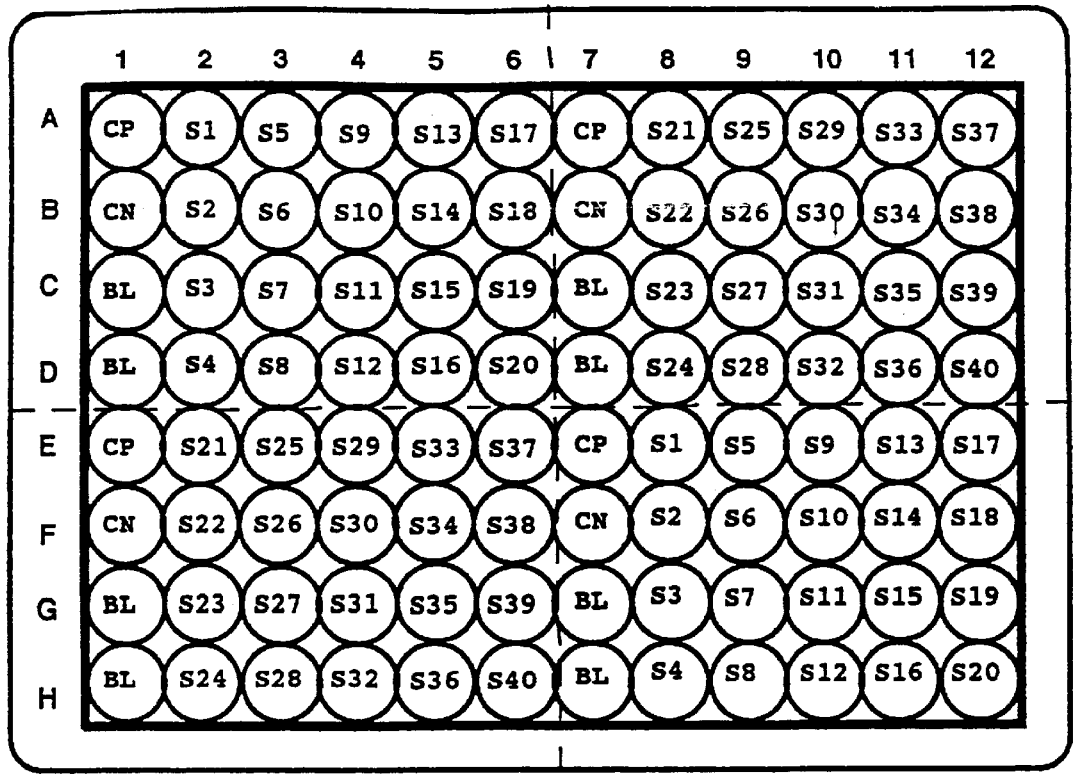
FIG. 1 illustrates the layout of the plate of the preferred kit of the present invention.

The kits of the present invention are novel in that they allow for a simple and fast testing in the field where the animals are. These kits are sufficiently stable that they have a shelf life of at least 25 weeks. The antigen was purified according to a novel procedure which allows for an increased sensitivity.

In the prior art, once the antigen was bound to the plate, this antigen was not stable very long. To the opposite, the antigen, once bound to the plate and once the HRP conjugate stabilizing solution (sold by Calbiochem-Novabiochem Corporation, La Jolla, Calif. 92039, U.S.A., catalogue #516534, i.e. phosphate buffered saline pH 7.2, containing BSA, 0.1% thimerosal and caprylic acid) has been added thereto, in accordance with the present invention, is stable for a long time. In fact, the antigen will remain stable for at least 25 weeks or until use.

The kits of the present invention are based essentially on the particular combination of a novel method of purification of lipopolysaccharide antigen from a reference strain of *A. pleuropneumoniae* serotype 5 antigen and a novel coating and stabilization of the antigen on the surface of the plate. The kit in accordance with the present invention is very specific, sensitive and stable. The test in accordance with the kit of the present invention consists in the determination of the presence or absence of anti-*A. pleuropneumoniae* antibodies in the serum of pigs for the serodiagnosis of *A. pleuropneumoniae* serotypes 5a and 5b.

The test essentially consists in the following steps:

a) A plate of 96 wells sensitized with the specific antigen of *A. pleuropneumoniae* serotype 5 is washed with a PBS-TWEEN™-20 buffer solution (TWEEN™-20: ICI Americas Inc., Delaware, USA).

b) A-serum sample of each pigs from the tested herds is distributed in two sensitized wells of step a). During this first incubation, the anti-*A. pleuropneumoniae* serotypes 5a and 5b antibodies, if present in the sera, will bind to the antigen attached to the plate or solid phase bound.

c) The plate is washed to remove from the wells any unbound material. A peroxidase-anti-IgG conjugate is added to each well, preferably obtained from Jackson Immuno Research Laboratories (catalogue #114-035-003). This conjugate binds to any IgG which would have bound to the antigen attached to the plate in step b). If the pig serum did not contain any anti-*A. pleuropneumoniae* serotypes 5a and 5b antibodies, the conjugate will remain free or in suspension and will be eliminated during this washing step.

d) The presence of immobilized peroxidase within the bound conjugate is revealed by the addition of a chromogen substrate 3,3',5,5'-tetramethylbenzidine, e.g. TMBLue™ (sold by Transgenic Science Inc., Milford' Mass. 01757, U.S.A., catalogue #TM-102, see U.S. Pat. No. 5,013,646, issued May 7, 1991). If the conjugate is present, there will be an oxidation reaction and a blue color will appear.

The preferred kit of the present invention comprises the following items:

1—Five 96-well plates (Nunc™, sold by Gibco, Burlington, Ontario, Canada, L7P 1A1) sensitized and stabilized with the purified antigen in accordance with the present invention.

2—Positive control; five vials containing each 0.4 ml of lyophilized serum from pigs experimentally inoculated with a strain of *A. pleuropneumoniae* serotype 5.

3—Negative control; five vials containing each 0.4 ml of lyophilized pig serum from a specific pathogen free herd.

4—Weak positive control; five vials containing each 0.4 ml of lyophilized serum from pigs experimentally inoculated with a strain of *A. pleuropneumoniae* serotype 5.

5—Conjugate; five vials of pig anti-IgG immunoglobulins coupled to peroxidase. Each vial contains 1.2 ml of lyophilized conjugate.

6—3,3',5,5'-tetramethylbenzidine, e.g. TMBLue™; five vials containing each 10 ml of 3,3',5,5'-tetramethylbenzidine, e.g. TMBLue™.

FIG. 1 illustrates the layout of the plate of the preferred kit of the present invention, where 40 different sera are analyzed. The wells are identified as follows:

BL=Blanks, PBS-TWEEN™-20 buffer solution (4 wells)
CP=Positive control, item #2 above (4 wells)
CN=Negative control, item #3 above (4 wells)
CPFA=Weak positive control, item #4 above (4 wells)
S1 to S40=serum to be analyzed, 2 wells for each serum.

Preparation of the PBS-TWEEN™-20 Buffer Solution

Add the following to 3 L of distilled water,
52.59 g of sodium chloride;
1.47 g of monobasic sodium phosphate;
7.02 g dibasic sodium phosphate;
1.5 ml of TWEEN™-20.

Mix well until a complete dissolution is achieved. Verify the pH, which should be about 7.30±0.05, if different adjust the pH using dibasic sodium phosphate. This solution has a shelf life of 1 week when kept at 4° C. The buffer solution should always be brought to room temperature before being used in the test.

Bacterial Strain

The strain of *A. pleuropneumoniae* serotype 5, referred to as strain 81–750, was used for the antigen production (Goyette G. et al., 1986, *Int. Pig. Vet. Soc. Proc.*, 9:258). The strain was kept lyophilized.

Bacterial Culture

The content of a vial was resuspended in one ml of PPLO (Difco Laboratories, Detroit, Mich.) liquid medium and inoculated to exhaustion on a PPLO agar plate. The plate was incubated aerobically for 24 hours at 37° C. A few colonies were resuspended in 5 ml of PPLO liquid medium. PPLO plates were inoculated at confluence with a sterile swab, these plates were then incubated 6 hours at 37° C. After the incubation, the bacterial growth was harvested by adding 3.0 ml of phosphate-buffered saline (PBS, pH 7.4) (Oxoid Ltd., Basingstoke, England) containing 0.5% (vol/vol) of formaldehyde (Fisher Scientific, Fair Lawn, N.J.) to each gel plates.

Antigen Purification

The bacterial suspension obtained was placed in a sterile bottle and was allowed to stand overnight at 4° C. The optical density was adjusted to 10.0 with a solution of PBS-0.5% formaldehyde. The suspensions were separated in sterile screw cap vials and boiled 60 min. Then the suspensions were centrifuged at 12,000×g for 30–40 min., 4° C. The supernatants were collected and filtered on a 0.22 μm pore size filter (Millipore Corp., Bedford, Mass.).

The antigen was purified according to the following procedure.

Preparing the phenol solution by mixing 90 g of phenol crystals with 100 ml of distilled water.

Mixing an equal volume of the phenol solution with an equal volume of the crude extract in Corex™ tubes, mixing by inversion and let stands for 30 min. at room temperature.

Centrifuged at 12,000×g, 4° C. for 30 min.

After the first centrifugation, two phases were obtained with an interface of insoluble material. The aqueous phase was collected with a Pasteur™ pipette and the volume was measured in a graduated cylinder.

Mixing an equal volume of the aqueous phase (first extraction) with an equal volume of the phenol phase in Corex™ tubes, mixing by inversion and let stands for 30 min. at room temperature.

Centrifuged at 12,000×g, 4° C. for 30 min.

The aqueous phase was collected and the volume was measured in a graduated cylinder.

Mixing an equal volume of the aqueous phase (second extraction) with an equal volume of the phenol phase in Corex™ tubes, mixing by inversion and let stands for 30 min. at room temperature.

During this period, prepare the dialysis membrane by soaking in distilled water for a sufficient period of time.

Centrifuged at 12,000×g, 4° C. for 30 min.

The aqueous phase was collected and the volume was measured in a graduated cylinder.

The aqueous phase (third extraction) was dialyzed against 3×12 L of distilled water to remove traces of phenol, do not dialyze for more than 24 hours.

Antisera—Negative Control

Sera from several pigs were obtained at the slaughter from a specific pathogen free herd; the sera were mixed and thimerosal (sold by Sigma, St-Louis, Mo. 14508, U.S.A., catalogue #T-5125) was added to obtain a final concentration of 0.01%. No history of *A. pleuropneumoniae* was ever reported for this herd since at least four years. The sera were tested using the ELISA technique against all the *A. pleuropneumoniae* serotypes by the pleuropneumonia laboratory of the Veterinary Medicine Faculty of University of Montreal.

Antisera—Positive Control

The strain *A. pleuropneumoniae* serotype 5 (strain 81–750) was used for the bacterial production. The content of a vial was resuspended in one ml of PPLO (Difco Laboratories, Detroit, Mich.) liquid medium and inoculated to exhaustion on two PPLO agar plates. The plates were incubated.aerobically for 18 hours at 37° C.

The bacterial production for the immunization of pigs was effected according to the following procedure.

Collecting a few colonies isolated with a sterile swab and resuspending them in a PPLO broth.

5 PPLO agar plates were inoculated at confluence with the broth and sterile swabs. One Mueller-Hinton agar plate was inoculated with the remaining broth to serve as a negative control. One PPLO agar plate was inoculated to exhaustion.

These plates were then incubated 18 hours at 37° C. One plate is used for serotyping.

After the incubation, harvesting the bacterial growth by adding 3.0 ml of PBS-0.5% formaldehyde to each plate, and mixed with a hockey stick made of sterile Pasteuru™ pipette and recovering the suspension with a pipette.

The bacterial suspension obtained was placed in a sterile bottle, mixed well and incubated 18 hours at room temperature.

The optical density was read at 540 nm and adjusted to 1.0 with a solution of PBS-0.5% formaldehyde.

The solution was kept at 4° C. until usage or for a maximum of one week.

For the immunization, four five-week old piglets were obtained from a specific pathogen free herd. No history of *A. pleuropneumoniae* was ever reported for this herd since at least four years and no pulmonary lesions were observed at the slaughter. At their arrival, the general state of health of the piglets is verified. The piglets are fed on demand with introductory fattening food for pigs (15/30 CO-OP). After a few days of adaptation, a blood sample is taken from each animal. The sera were tested using the ELISA technique against all the *A. pleuropneumoniae* serotypes by the pleuropneumonia laboratory of the Veterinary Medicine Faculty of University of Montreal. The sera were negative for all serotypes.

The pigs were immunized intravenously with 0.5 ml of the bacterial suspension every three weeks and this until the ELISA titer give a value superior or equal to 1.0 with the serum diluted 1/200. The pigs were bled and the serum of each animal was mixed together.

ELISA

For evaluating the efficiency and reliability of the kits of the present invention, two methods of ELISA were used. In the first method, the plates are used immediately after sensitization, the incubation period are of one hour and ABTS (2,2'-azino-bis(3-ethylbenzthiazoline)-6-sulfonic acid) is used as a chromogen. In the second method, the plates are treated with HRP conjugate stabilizing solution (sold by Calbiochem-Novabiochem Corporation, La Jolla, Calif. 92039, U.S.A., catalogue #516534, i.e. phosphate buffered saline pH 7.2, containing BSA, 0.1% thimerosal and caprylic acid) after sensitization, the incubation period are of 15 min. and 3,3',5,5'-tetramethylbenzidine, e.g. TMBLue™ is used as a chromogen.

The ELISA consists in:

1—Sensitization of the Plates

Diluting in 150 μl of antigen in 75 ml of PBS-EDTA buffer, pH 7.3.

Add 100 μl of antigen to each well.

Seal the plate with an acetate sheet.

Incubate overnight at 4° C.

For the evaluation of the kit, for the stability assays as well as for the visual assays, the plates are treated with HRP conjugate stabilizing solution (sold by Calbiochem-Novabiochem Corporation, La Jolla, Calif. 92039, U.S.A., catalogue #516534, i.e. phosphate buffered saline pH 7.2, containing BSA, 0.1% thimerosal and caprylic acid) The content of the wells are emptied and 100 μl of HRP conjugate stabilizing solution is added to each well. The plates containing the HRP conjugate stabilizing solution are kept at 4° C. until needed.

2—Washing of the Sensitized Plates

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

3—Sera Preparation

The sera are diluted 1/200 in PBS-TWEEN™-20 buffer and distributed in the amount of 100 μl to each well.

Gently shake the plate to ensure the distribution of the samples at the bottom of the wells. Cover the plate with an acetate sheet.

Let the plate stand for one hour at room temperature for ELISA using ABTS or for 15 min. between 18° C. and 22° C. for ELISA using TMBLue™.

4—Washing of the Plate to Remove Unbound Antibodies

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

5—Distribution of Conjugate

The conjugate consists in horseradish peroxidase-labeled immunoglobulin G fraction of rabbit antiserum raised against porcine IgG (Jackson Immuno Research Laboratories Inc., catalogue #114-035-003). The conjugate is used at a final dilution of 1/6000. The conjugate is distributed in the amount of 100 μl to each well of the plate.

Gently shake the plate to ensure the distribution of the samples at the bottom of the wells. Cover the plate with an acetate sheet.

Let the plate stand at room temperature for one hour for ELISA using ABTS or for 15 min. for ELISA using TMBLue™.

6—Washing of the Plate to Remove Unbound Conjugate

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

ELISA Using ABTS

This was used only to validate the kit of the present invention or to get a spectrophotometer value.

7a—Preparation and Distribution of Chromogen

The reaction was visualized using 2 mM $H_2O_2$ and 0.4 mM ABTS (2,2'-azino-bis(3-ethylbenzthiazoline)-6-sulfonic acid) (Sigma Chemical) in 50 mM citrate solution (pH 4.0). Add 100 µl of this citrate-ABTS solution to each well of the plate.

Gently shake the plate to ensure the distribution of the samples at the bottom of the wells.

Let the plate stand for 30 min. at room temperature (between 18° C. and 22° C.).

8a—Reading and Results Interpretation

The optical density was read at 410 nm using an automated plate reader (MR5000™, Dynatech Laboratories Inc.).

The results were calculated according to the following procedure.

1—The values of the eight wells BL (blank) were verified:

A value inferior to 0.08 indicates a valid test, continue the reading.

A value superior to 0.08 indicates an invalid test, repeat the test with a new kit or contact the kit manufacturer.

2—The mean values of the negative and positive controls are calculated as follows (see FIG. 1 for identification of wells):

Positive control=$((A1+E1+A7+E7)/4)-BL$ mean

Negative control=$((B1+F1+B7+F7)/4)-BL$ mean

3—The color of the CPFA (weak positive control) is verified; it should be light blue.

4—The answer of each sample should be quantified as follows:

0=colorless well or slightly bluish

1+=well of a light blue color

2+=well of a blue color

3+=well of a dark blue color

4+=well of a dark blue color

The reading with a spectrophotometer was effected and calculated as described in section 8a above.

RESULTS

Reproducibility of the Antigen Attachment

The aim of this test series consists in verifying the reproducibility of the antigen bounding at the bottom of the wells of the plate. The variation in the antigen attachment between the wells of a same plate was determined. Each of the 96 wells of each three plates was sensitized with 10 µg of A. pleuropneumoniae serotype 5 antigen, the plates were used immediately after their sensitization according to the ELISA-ABTS procedure. The control sera were distributed in the three plates. The positive control serum was used in 17 wells of each three plates and the negative control serum in 16 wells. Each of the six control serum fields was distributed in eight wells of each plate. The results are presented in Table 1. The intra- and inter-plate variation was inferior to 16%.

TABLE 1

| | Plate #1 | | | Plate #2 | | | Plate #3 | | | Mean of the three plates | | |
| --- | --- | --- | --- | --- | --- | --- | --- | --- | --- | --- | --- | --- |
| Serum | Mean | Standard deviation | Deviation % | Mean | Standard deviation | Deviation % | Mean | Standard deviation | Deviation % | Mean | Standard deviation | Deviation % |
| B | 0.050 | 0.003 | 6 | 0.044 | 0.002 | 4 | 0.045 | 0.006 | 13 | 0.045 | 0.005 | 11 |
| CN | 0.090 | 0.007 | 7 | 0.116 | 0.009 | 7 | 0.106 | 0.008 | 7 | 0.104 | 0.013 | 12 |
| CP | 1.074 | 0.035 | 3 | 1.262 | 0.045 | 3 | 1.183 | 0.045 | 4 | 1.173 | 0.094 | 8 |
| EP1 | 0.986 | 0.042 | 4 | 1.121 | 0.031 | 3 | 1.058 | 0.073 | 7 | 1.055 | 0.067 | 6 |
| EP2 | 0.596 | 0.031 | 5 | 0.685 | 0.033 | 5 | 0.625 | 0.063 | 10 | 0.635 | 0.045 | 7 |
| EN1 | 0.102 | 0.010 | 9 | 0.138 | 0.011 | 8 | 0.123 | 0.005 | 4 | 0.121 | 0.018 | 14 |
| EN2 | 0.161 | 0.011 | 6 | 0.226 | 0.012 | 5 | 0.205 | 0.025 | 12 | 0.197 | 0.033 | 16 |
| ED1 | 0.265 | 0.012 | 4 | 0.322 | 0.021 | 6 | 0.298 | 0.009 | 3 | 0.295 | 0.028 | 9 |
| ED2 | 0.241 | 0.015 | 6 | 0.303 | 0.012 | 4 | 0.280 | 0.025 | 9 | 0.274 | 0.031 | 11 |

ELISA Using TMBLue™ in Accordance With the Present Invention

7b—Preparation and Distribution of Chromogen

Add 100 µl of TMBLue™ to each well of the plate.

Gently shake the plate to ensure the distribution of the samples at the bottom of the wells.

Let the plate stand for 5 min. at room temperature (between 18° C. and 22° C.).

8b—Reading and Results Interpretation

The visual reading was effected without any reading instruments as follows:

The results were calculated according to the following procedure.

1—The color of the eight wells BL (blanks) and of the negative controls is verified; it should be colorless.

2—The color of the positive controls is verified; it should be dark blue.

SPECIFICITY AND SENSITIVITY OF THE KIT

The specificity of the antigen was verified using sera from pigs experimentally infected with strains of A. pleuropneumoniae of different serotypes or with other types of bacteria. The ELISA method was used with ABTS as a chromogen.

The antigen gave positive reactions with sera from pigs experimentally infected with strains of A. pleuropneumoniae of serotypes 5a and 5b, and negative reactions with sera from pigs experimentally infected with strains of A. pleuropneumoniae of serotypes 1, 2, 3, 4, 7, 9 and 11 (Table 2). The sera from pigs inoculated with H. parasuis, P. multocida, E. coli, Bordetella bronchoseptica, Mycoplasma hyorhinis or A. suis gave negative reactions.

TABLE 2

ELISA results of the antigen purified from
*A. pleuropneumoniae* serotype 5 against different sera of
pigs inoculated experimentally

| Sera from pigs inoculated with | Optical density |
|---|---|
| *A. pleuropneumoniae* serotype 1 (strain Shope 4074) | 0.09 |
| *A. pleuropneumoniae* serotype 2 (strain 4226) | 0.08 |
| *A. pleuropneumoniae* serotype 3 (strain 1421) | 0.10 |
| *A. pleuropneumoniae* serotype 4 (strain M62) | 0.06 |
| *A. pleuropneumoniae* serotype 5a (strain K17) | 1.12 |
| *A. pleuropneumoniae* serotype 5b (strain 81-750) | 1.10 |
| *A. pleuropneumoniae* serotype 7 (strain WF83) | 0.06 |
| *A. pleuropneumoniae* serotype 9 (strain CVJ 13261) | 0.08 |
| *A. pleuropneumoniae* serotype 11 (strain 56153) | 0.07 |
| *Actinobacillus suis* | 0.08 |
| *Haemophilus parasuis* | 0.07 |
| *Pasteurella multocida* | 0.01 |
| *Escherichia coli* | 0.01 |
| *Bordetella bronchoseptica* | 0.07 |
| *Mycoplasma hyorhinis* | 0.09 |

Secondly, the plates were treated with HRP conjugate stabilizing solution after the sensitization with the antigen and the ELISA-TMBLue™ technique was used (Table 3).

TABLE 3

ELISA-TMBLue ™ responses of the antigen purified from
*A. pleuropneumoniae* serotype 5a against reference sera

| Serum used | Optical density | Visual Response |
|---|---|---|
| CN | 0.063 | 0 |
| CP | 1.471 | 4+ |
| EP1 | 1.141 | 3+ |
| EP2 | 0.570 | 2+ |
| EN1 | 0.064 | 0 |
| EN2 | 0.124 | 0 |
| ED1 | 0.240 | 1+ |
| ED2 | 0.175 | 1+ |

The CP, EP1 and EP2 sera gave positive responses. The CP serum came from a pool of sera obtained following the inoculation of two five weeks old piglets with the reference strain of *A. pleuropneumoniae*. The EP1 and EP2 sera were obtained from animals of a herd showing an acute infection and wherein mortality to *A. pleuropneumoniae* serotype 5 is frequently observed. The CN, EN1 and EN2 sera gave negative responses. The CN serum came from a pool of pig sera taken from a SPF (specific pathogen free) herd for which no history of pleuropneumonia, at the slaughter house, had been reported for at least four years. The EN1 and EN2 sera came from pigs from two herds with no history of pleuropneumonia and without lesions at the slaughter house. The ED1 and ED2 sera gave weak positive responses by ELISA. These sera were obtained from two pigs from a herd chronically infected with *A. pleuropneumoniae* serotype 5. These two sera are considered weak positives; they have indeed been classified by the service of pleuropneumonia of the Veterinary Medicine Faculty (VMF) of the University of Montreal as weakly positive sera by the ELISA reference test.

STUDY OF THE STABILITY OF THE KIT

During the preliminary trials, different techniques of antigen attachment, different buffers, as well as different methods of preservation of the plates were evaluated. The chosen method with respect to the antigen attachment consists in diluting 150 μl of antigen in 75 ml of PBS-EDTA buffer, pH 7.3. 100 μl of this solution are then distributed in each well of the 96-well plates (Nunc™), and the plates are incubated 18 hours at 4° C. The content of the plates is emptied and 100 μl of HRP conjugate stabilizing solution is added to each well. The plates are kept at 4° C. The stability of the plates is assessed monthly. In addition to the three controls included in the kit, eight additional sera are used for the stability study. These sera are kept at −20° C. and a new aliquot is used for each assay. The kit is validated as described in the protocol of utilization. As shown in Table 4, the kit is stable for at least 12 weeks.

TABLE 4

Stability assessment of the visual test kit for
*A. pleuropneumoniae* serotype 5a/5b

| | Number of weeks at 4° C. | | | | | | |
|---|---|---|---|---|---|---|---|
| Sera | 0 | 4 | 8 | 12 | 16 | 20 | 24 |
| Positives (4+, 3+, 2+) | 5* | 5 | 5 | 5 | 5 | 5 | 5 |
| Weak positives (1+) | 1 | 1 | 1 | 1 | 1 | 1 | 1 |
| Negatives (0+) | 5 | 5 | 5 | 5 | 5 | 5 | 5 |

*Number of sera

REPRODUCIBILITY OF THE KIT DEPENDING ON THE USER

One lot of three complete kits were prepared. Twenty (20) different sera were obtained from the serology laboratory of the VMF; one kit as well as one aliquot of each undiluted serum was given to three different users. Identical results were obtained by the three different users (Table 5).

TABLE 5

Evaluation of the visual test kit for *A. pleuropneumoniae*
serotype 5a/5b by three different users

| | batch | | |
|---|---|---|---|
| Sera | User #1 | User #2 | User #3 |
| Positives (4+, 3+, 2+) | 3* | 3 | 4 |
| Weak positives (1+) | 4 | 4 | 3 |
| Negatives (0+) | 16 | 16 | 16 |

Number of sera

Finally in order to verify the sensitivity and the specificity of the kit of the present invention, several complete kits were prepared. A total of 316 sera were obtained from the pleuropneumonia serology laboratory of the Veterinary Medicine Faculty of the University of Montreal. These sera had been classified by this laboratory and had been obtained from herds having a well known sanitary status. The 192 sera classified as negative by the pleuropneumonia serology laboratory were confirmed as negative with the kit of the present invention. Within the sera classified as positive by the pleuropneumonia serology laboratory, 23 sera gave a 1+ response with the kit of the present invention and the remaining 101 sera gave a 2–4+ response therewith (Table 6).

TABLE 6

Sensitivity and specificity of the visual test kit for A. pleuropneumoniae serotype 5a/5b

| Results with the kit | Results with the "golden test" | |
| --- | --- | --- |
|  | Positive | Negative |
| 4–3+ | 54 | 0 |
| 2+ | 47 | 0 |
| 1+ | 23 | 0 |
| 0 | 0 | 192 |

DISCUSSION

The determination of the sensitivity and the specificity of a test is carried out either by using animal populations having a status which is clearly identified as "infected" or as "healthy" or by comparing the results of the test with a reference test, a "golden test". In accordance with the present invention, both methods were used.

As sera of well defined status, 15 sera from pigs infected experimentally with strains of A. pleuropneumoniae of different serotypes or with different bacteria were used. Thereafter, eight additional sera of pigs of well defined status were used; one serum came from a pig infected experimentally with A. pleuropneumoniae serotype 5 (strain 87–750), one serum came from a pool of sera of specific pathogen free pigs (SPF) and six pig sera of came from pigs belonging to different herds having a well defined status.

The ELISA kit of the present invention gave a positive response only with sera from pigs infected experimentally or naturally with A. pleuropneumoniae serotype 5. The sera of pigs infected experimentally with strains of A. pleuropneumoniae serotypes 1, 2, 3, 4, 7, 9 and 11; H. parasuis, P. multocida, E. coli, Bordetella bronchoseptica, Mycoplasma hyorhinis or A. suis, as well as the two pools of sera from SPF pigs gave negative responses. The ED1 and ED2 sera came from pigs having no clinical sign of pleuropneumonia but evidence of infection with A. pleuropneumoniae serotype 5 had been observed in the herd. These sera were thus considered as weakly positive.

The ELISA kit of the present invention is stable at 4° C. for at least 12 weeks. The stability studies are still in progress.

The specificity and sensitivity of the kit of the present invention was also evaluated using 316 pig sera. These sera were furnished by the pleuropneumonia laboratory of the Veterinary Medicine Faculty of the University of Montreal. This laboratory was considered as the laboratory of reference with respect to the serology of Actinobacillus pleuropneumoniae and the results obtained by this laboratory were considered as the "golden test". This laboratory has been analyzing between 30,000 and 40,000 pig sera per year for more than 10 years. The methodology used by the pleuropneumonia laboratory consists in an ELISA technique standardized in order to determine the presence of antibodies. A complement fixation test is no longer in use in this laboratory, due to its lack of sensitivity and specificity. The serology laboratory has developed its standardized ELISA test by comparing different types of antigen (Gottschalk, M. et al., 1994, Vet. Microbiol., 42:91–104). In view of the great numbers of sera received by this laboratory, the results obtained thereby were considered as a reference. The status of the sera as obtained by this laboratory, whether positive or negative, was thus well certified. The specificity and sensitivity of the kit was evaluated using 295 pig sera. A correlation of 100% was observed between the results obtained with the kit of the present invention and the classification form the serology laboratory. All the sera classified as negative by the reference serology laboratory were thus determined as negative by the kit of the present invention. If one considers the weak positives or positives 1+ as positives, all the sera classified as positive by the reference laboratory gave a positive response using the kit of the present invention.

The kit of the present invention differs from the ELISA method used by the reference serology laboratory. In the method used by the latter, the antigen is fixed to the plates in a PBS buffer and the plates are used immediately following the antigen fixation. In addition, the serology laboratory utilizes a computerized reading protocol for the determination of the antibodies in the samples (Trottier, Y. L. et al., 1992, J. Clin. Microbiol., 30:46–53).

In the case of the kit of the present invention, the antigen is purified using a higher concentration of phenol and the antigen fixation is different. Indeed, the purified antigen is resuspended in a PBS-EDTA buffer which is then added to the wells of the plates. Following an 18 h incubation, HRP conjugate stabilizing solution is added to each well. The antibodies in the samples are then determined visually by adding a chromogen, preferably TMBlue™.

When compared to the standardized ELISA method used by the serology laboratory, the kit of the present invention, demonstrates a sensitivity and a specificity of 100%. In addition, The kit of the present invention is faster to use than the ELISA-ABTS method of the prior art. Indeed, using the kit of the present invention, results are obtained in less than one hour while a minimum of three hours are required for the ELISA-ABTS method in addition to the overnight step required for the fixation of the antigen. Furthermore, ABTS is considered as potentially carcinogenic in addition to being only moderately stable.

The kit of the present invention is easily used and provides rapid results. The kit can be used by a veterinarian having a minimum of experience, it may be used in the field where the animals are kept and does not require laboratory skills, since only simple steps need to be performed. In addition, this kit was demonstrated to give highly reliable and reproducible results independently of the user. The results obtained with the kit of the present invention are identical to those obtained by the pleuropneumonia laboratory of the VMF. The kit of the present invention is thus highly advantageous as compared to the presently available laboratory tests with respect to its rapidity, reliability, sensitivity, specificity, stability and cost.

We claim:

1. An enzyme-linked immunosorbent assay (ELISA) diagnostic kit for the assay of A. pleuropneumoniae serotypes 5a and 5b antibodies in the serum of a pig comprising in separate packaging:

a) a solid support having bound thereto a purified lipopolysaccharide A. pleuropneumoniae serotype 5 antigen for a specific binding to anti-A. pleuropneumoniae serotypes 5a or 5b antibodies present in the serum of the pig, said bound antigen being stabilized for at least 25 weeks at 4° C. with phosphate buffered saline pH 7.2, containing BSA, 0.1% thimerosal and caprylic acid; and b) a detectably labeled conjugate which binds to the anti-*A. pleuropneuizlolniae* serotypes 5a or 5b antibodies bound to said antigen which is bound to said solid support.

2. The kit of claim 1, which further comprises the following:
   c) a substrate which allows for the visualization of the detectably labeled conjugate.

3. The kit of claim 2, wherein said detectably labeled conjugate comprises an enzyme label.

4. The kit of claim 3, wherein said substrate is a composition for providing a colorimetric, fluorimetric or chemiluminescent signal in the presence of said enzyme label.

5. The kit of claim 3, wherein said detectably labeled conjugate comprises pig anti-IgG immunoglobulins coupled to peroxidase.

6. The kit of claim 4, wherein said colorimetric composition is 3,3',5,5'-tetramethylbenzidine.

7. The kit of claim 1, wherein said solid support is a 96-well plate.

8. An enzyme-linked immunosorbent assay (ELISA) diagnostic kit for the assay of *A. pleuropneumoniae* serotype 5a and 5b antibodies in the serum of a pig comprising in separate packaging the following:
   a) a solid support having bound thereto a purified lipopolysaccharide *A. pleuropneumaniae* serotype 5 antigen for a specific binding to anti-*A pleuropneumaniae* serotypes 5a and 5b antibodies present in the serum of the pig, said bound antigen being stabilized for at least 25 weeks at 4° C. with phosphate buffered saline pH 7.2, containing BSA, 0.1% thimerosal and caprylic acid;
   b) a positive control vial of serum from a pig experimentally inoculated with a strain of *A. pleuropneumoniae* serotype 5;
   c) a negative control vial of pig serum from a *A. pleuropneumoniae* free herd;
   d) a weak positive control vial of serum from a pig experimentally inoculated with a strain of *A. pleuropneumoniae* serotype 5;
   e) a conjugate vial of pig anti-IgG immunoglobulins coupled to peroxidase; and
   f) a calorimetric composition consisting of 3,3',5,5'-tetramethylbenzidine or 2,2'-azino-bis(3-ethylbenzthiazoline-6-sulfonic acid).

9. The kit of claim 8, wherein any of said positive or negative control serum is lyophilized serum.

10. The kit of claim 9, wherein said lyophilized serum, before lyophilization, is in the amount of about 0.4 ml of positive or negative control serum.

11. A method for the preparation of the kit of claim 1, which comprises the steps of:
   a) purifying lipopolysaccharide *A. pleuropneumoniae* serotype 5 antigen by phenol extraction of a crude extract containing the antigen, whereby an aqueous phase containing the antigen is produced, centrifugation of said crude extract and collecting the aqueous phase containing the antigen;
   b) fixing the antigen of step a) to a solid support and adding phosphate buffered saline pH 7.2, containing BSA, 0.1% thimerosal and caprylic acid to stabilize said fixed antigen, wherein said fixed antigen is stable for at least 25 weeks at 4° C.;
   c) immunizing a pig with a strain of *A. pleuropneumoniae* serotype 5 and collecting serum to serve as positive control sera; and
   d) collecting sera from *A. pleuropneumoniae* free herds to serve as negative control sera.

12. The method of claim 11, wherein the crude extract is phenol extracted at least one time with an equal volume of phenol 90% (weight/volume) to obtain aqueous and phenol phases containing the antigen from the phenol phase and dialysis of the aqueous phase to eliminate traces of phenol.

13. The method of claim 11, wherein the step b) is effected by incubating the aqueous phase containing the antigen obtained from step a) with the solid support overnight at 4° C., wherein said solid support is incubated with phosphate buffered saline pH 7.2, containing BSA, 0.1% thimerosal and caprvlic acid to stabilize the fixed antigen.

14. The kit of claim 1 further comprising at least one of the following:
   c) serum from pigs experimentally inoculated with a strain of *A. pleuropneumoniae* serotype 5 to serve as a positive control; and
   d) pig serum from a specific pathogen free herd to serve as a negative control.

15. The kit of claim 14 which contains the serum that serves as the negative control in a lyophilized form.

16. The kit of claim 15 wherein the serum is in the amount of about 0.4 ml of lyophilized serum.

17. A soiId support for use in an assay of *A. pleuropneumornae* serotypes 5a or 5b antibodies in the serum of pigs having bound thereto a purified lipopolysaccharide *A. pleuropneumoniae* serotypes 5a or 5b unreacted antigen for a specific binding to anti-*A. pleuropneumoniae* serotypes 5a or 5b antibodies present in the serum of pigs, wherein the bound antigen is storotred in phosphate buffered saline pH 7.2, containing BSA, 0.1% thimerosal and caprylic acid, which keeps said bound antigen stable for at least 25 weeks at 4° C.

18. The solid support of claim 17 that is a 96-well plate.

\* \* \* \* \*